United States Patent [19]

Ellison

[11] Patent Number: 4,874,375
[45] Date of Patent: Oct. 17, 1989

[54] TISSUE RETRACTOR

[76] Inventor: Arthur E. Ellison, Adams Rd., Williamstown, Mass. 01267

[21] Appl. No.: 37,841

[22] Filed: Apr. 13, 1987

[51] Int. Cl.$^4$ .............................................. A61M 5/18
[52] U.S. Cl. ................................ 604/164; 128/303 R; 128/330; 128/20
[58] Field of Search ............... 604/164, 264, 289; 128/3, 20, 304, 305, 330

[56] References Cited

U.S. PATENT DOCUMENTS

| | | | |
|---|---|---|---|
| 1,059,631 | 4/1913 | Popovics | 128/330 |
| 1,798,124 | 3/1931 | Hunn | 128/20 |
| 1,867,624 | 7/1932 | Hoffman | 128/784 |
| 2,811,971 | 11/1957 | Scott | 128/335 |
| 3,001,522 | 9/1961 | Silverman | 128/2 |
| 3,040,739 | 6/1962 | Grieshaber | 128/20 |
| 3,404,677 | 10/1968 | Springer | 128/2 |
| 3,406,685 | 10/1968 | May | 604/164 |
| 3,410,269 | 11/1968 | Hovick | 128/361 |
| 3,716,058 | 2/1973 | Tanner | 128/337 |
| 3,774,606 | 11/1973 | Norton | 604/164 |
| 3,857,386 | 12/1974 | Ashbell | 128/20 |
| 3,929,123 | 12/1975 | Jamshidi | 128/2 B |
| 3,964,468 | 6/1976 | Schulz | 128/2 B |
| 3,995,619 | 12/1976 | Glatzer | 128/2 B |
| 4,051,844 | 10/1977 | Chiulli | 128/20 |
| 4,116,232 | 9/1978 | Rabban | 128/20 |
| 4,182,327 | 1/1980 | Haley | 128/215 |
| 4,200,111 | 4/1980 | Harris | 128/751 |
| 4,221,212 | 9/1980 | Miller | 128/330 X |
| 4,235,238 | 11/1980 | Ogui et al. | 128/334 R |
| 4,243,047 | 1/1981 | Olsen | 128/751 |
| 4,243,048 | 1/1981 | Griffin | 128/751 |
| 4,340,066 | 7/1982 | Shah | 128/304 |
| 4,378,019 | 3/1983 | Yamada | 128/330 |
| 4,382,444 | 5/1983 | Malmin | 128/330 |
| 4,392,495 | 7/1983 | Bayers | 128/334 R |
| 4,396,021 | 8/1983 | Baumgartner | 128/754 |
| 4,406,237 | 9/1983 | Eguchi et al. | 112/169 |
| 4,440,171 | 4/1984 | Nomoto et al. | 128/335.5 |
| 4,459,978 | 7/1984 | Kotsanis | 128/20 |
| 4,461,281 | 7/1984 | Carson | 128/305 X |
| 4,465,070 | 8/1984 | Eguchi | 128/334 R |
| 4,517,965 | 5/1985 | Ellison | 128/20 |
| 4,520,797 | 6/1985 | Petersen | 128/20 |
| 4,723,546 | 2/1988 | Zagorski | 128/305 |

OTHER PUBLICATIONS

Arthroscopic Retractor, Techmedia, Inc., advertisement.
John B. McGinty, M.D., "Arthroscopy of the Knee: Update and Review", Orthopedics Digest, Nov.-Dec., 1979, 7:17-35.

Primary Examiner—John D. Yasko

[57] ABSTRACT

An improved tissue retractor serves as a multifunctional surgical instrument particularly adapted for use during arthroscopic surgery. The instrument is preferably capable of putting tissue into tension either in a direction toward the arthroscopic portal or away from the portal. When tensioning toward the portal, the instrument acts as a tissue retractor. When tensioning away from the portal, the instrument acts as a distender or stretcher of tissue. The instrument includes a pointed obturator slidingly contained within a hollow sheath. The obturator includes a reduced cross-sectional area near the pointed end which acts as a barb when retracting tissue. In one embodiment, the hollow sheath has a bevelled, pointed end which disengages tissue from the obturator. A nozzle attached to the remote end of the hollow sheath may be attached to a syringe for introduction of fluid into the tissue. The instrument can also be used as a needle probe.

20 Claims, 4 Drawing Sheets

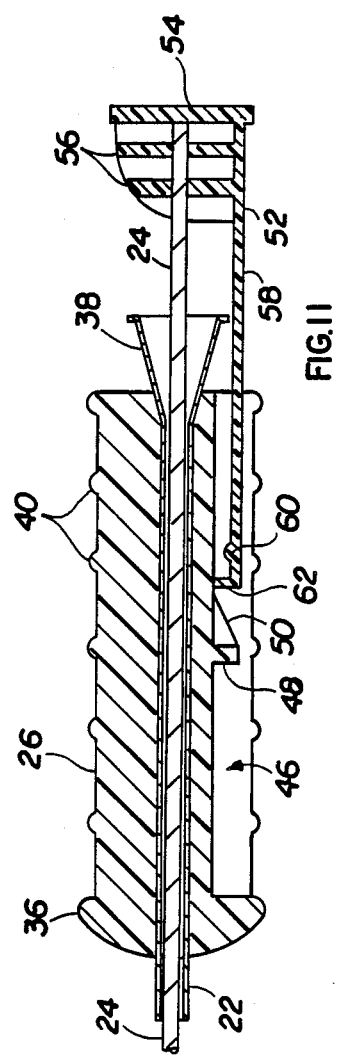
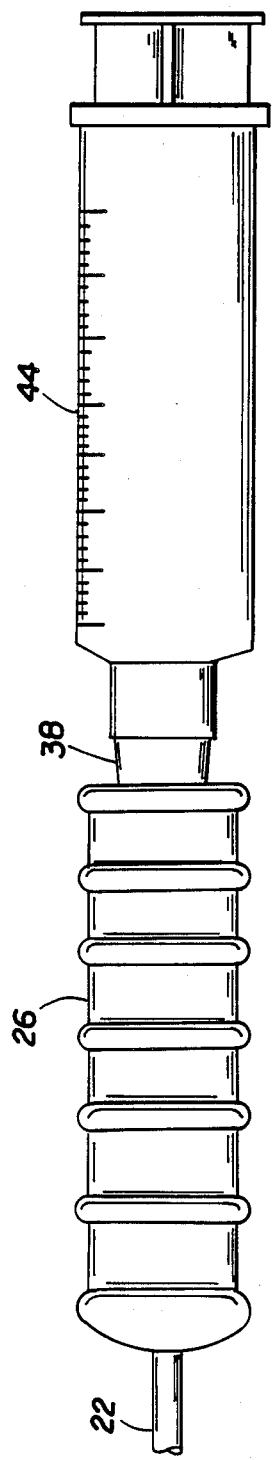
FIG.11
FIG.10

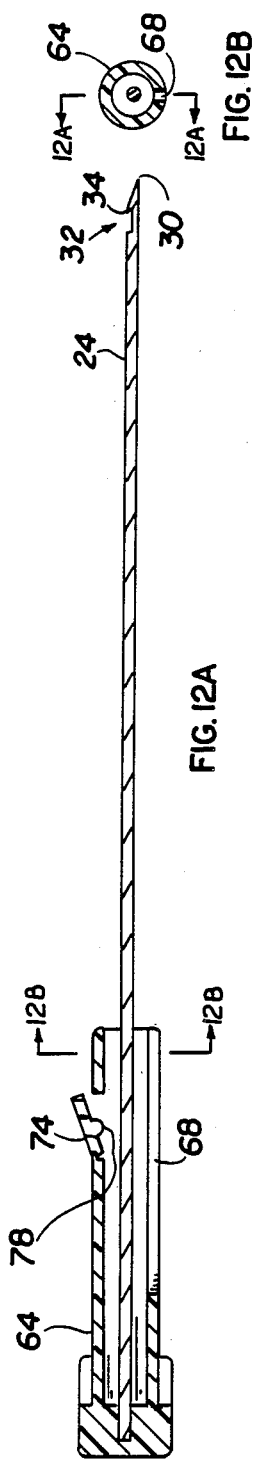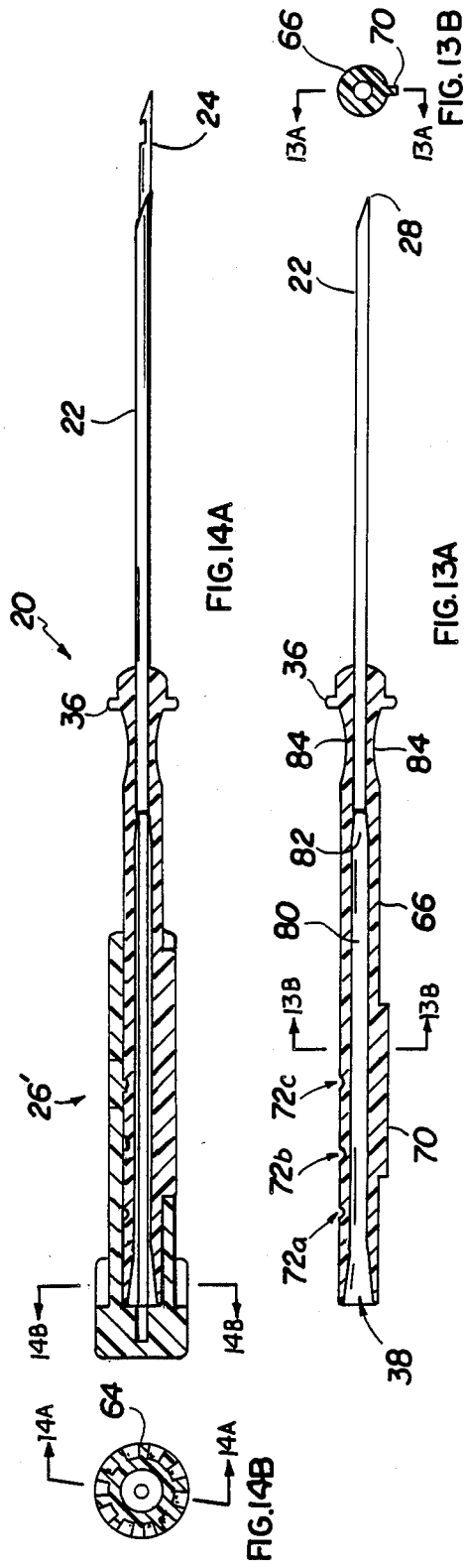

TISSUE RETRACTOR

BACKGROUND OF THE INVENTION

This invention relates to a surgical apparatus and more particularly to a surgical instrument for use during arthroscopic surgery, as on the knee joint.

The arthroscope is a small telescope-like device which can be inserted through a portal in the skin into an area such as a knee joint permitting visualization of conditions within the knee joint. The development of the arthroscope has led to arthroscopic surgery in which only small punctures are made in the skin covering the joint. Arthroscopic surgery has several advantages such as rapid return to preoperative activity. The use of very small incisions has an obvious cosmetic advantage, and this surgery has also resulted in low complication rates with a very low incidence of infection.

Because only very small incisions are made during arthroscopic surgery, it is oftentimes difficult to grab small tags and tabs of tissue. It is generally desirable to place tissue under tension, either in a direction toward or away from the arthroscopic portal, for making a subcutaneous cut, so that the cut is straight and clean. Again, because of the small incisions, it is often difficult to apply the desired tension.

During arthroscopic surgery, it is often desirable to introduce a needle, such as a spinal needle, to act as a probe in the vicinity of the surgery. The probe may pierce tissue and is useful in exploring the region prior to making larger incisions. Additionally, it is sometimes desirable to introduce a fluid into the joint being operated upon.

One instrument which is useful during arthroscopic surgery on the knee joint is my Tissue Retractor disclosed in U.S. Pat. No. 4,517,965 issued May 21, 1985. In that patent, I describe a tissue retractor which includes a rigid elongate sheath with a sharpened end which includes a retractable, laterally-projecting barb. The barb remains in a retracted position, flush with the sheath, until a rod is advanced in the sheath forcing the barb to project laterally. This invention requires manufacturing the barb member out of a surgical grade spring steel, along with very precise machining. The manufacture of the Tissue Retractor has proven rather expensive. Furthermore, my prior invention was only capable of the single function of retracting tissue, i.e., tensioning tissue in a direction toward the portal.

It is therefore an object of this invention to provide a surgical apparatus for use during arthroscopic surgery which is able to immobilize flaps and tags of tissue and put them under either retracting or stretching tension for cutting.

It is a further object of this invention to provide an apparatus which is capable of performing several functions within a single incision.

Another object is to provide an apparatus which is readily and accurately manipulated under arthroscopic visualization within a joint.

Yet another object is to provide an apparatus which is useful in introducing fluid into a joint.

It is still a further object to provide an apparatus which may be used as a probe within a joint.

Yet a further object is to provide an apparatus which is inexpensive and easy to fabricate.

Other objects will in part be apparent and in part pointed out hereinafter.

SUMMARY OF THE INVENTION

The multifunctional surgical instrument disclosed herein for use during arthroscopic surgery, particularly for surgery within the knee joint, includes a pointed obturator slidingly contained within a hollow sheath. The obturator has a sharp, pointed end which protrudes slightly from the sheath so that the obturator and sheath may together act as a needle when piercing tissue. This may be known as the "probe" mode of the invention. In one embodiment, the surface of the sheath and the surface of the pointed obturator cooperate to form a generally smoothly-shaped surface in the vicinity of the interface between the obturator and the sheath. This smoothly-shaped surface permits the instrument to pierce tissue or be withdrawn without catching either the obturator surface or the end of the sheath on the tissue.

A handle is attached to the end of the instrument which is remote from the knee joint. This handle preferably has a generally cylindrical shape which is comfortable to grasp and permits accurate control of the instrument. A finger stop at the end of the handle provides added control. The handle includes a latching device which fixes the axial position of the obturator within the sheath to maintain the smooth exterior surface of the invention when it is in the probe mode.

Near, but not at its pointed end, the obturator includes a reduced cross-sectional area. When the obturator is fixed within the sheath in the probe-mode position, this reduced cross-sectional area is fully enclosed by the sheath. In a preferred embodiment, the obturator and sheath both have a cylindrical shape, and the reduced cross-sectional area is provided by a notch within the obturator having a flat bottom surface. The surface of the obturator between the pointed end and the reduced cross-sectional area includes an acute angle which acts as a barb. By advancing the obturator out of the sheath and pressing it against tissue, the tissue is retained in the notch by the barb, and may be retracted. In this manner, the tissue is tensioned in a direction toward the arthroscopic portal. This may be known as the "retractor" mode of the invention.

Disengaging the tissue from the obturator consists of first, advancing the obturator while maintaining the position of the hollow sheath to relieve tension on the tissue. Then, the sheath is advanced to enclose the obturator while the position of the obturator is maintained. In one embodiment, the sheath has a bevelled end which may be used to further disengage tissue from the obturator when the sheath is advanced along the obturator.

The hollow sheath also includes a sharp end. This sharp end may include one or two points, or may take an annular shape. The sharp end can engage tissue and may be used to distend tissue when the obturator is removed from the sheath. In this manner, the tissue may be tensioned in a direction away from the arthroscopic portal. This may be known as the "distending" mode of the invention.

In a preferred embodiment, a nozzle is included as part of the handle. This nozzle is in fluid communication with the hollow sheath. When the obturator is fully withdrawn from the sheath, a syringe may be attached to the nozzle, and fluid such as a dye, a drug, or cleanser may be introduced into the joint. This may be known as the "fluid introducing" mode of the invention.

A principal advantage of the present invention lies in its multifunctional nature. The instrument may be used as a probe to pierce tissue. In conjunction with the arthroscope, the probe allows the surgeon to visualize and explore the inside of the knee joint prior to making larger incisions. By advancing the obturator relative to the sheath, the instrument becomes a tissue retractor. By withdrawing the obturator, at least partially from the sheath, the instrument becomes a tissue distender. Tensioning tissue by either retracting or stretching the tissue greatly facilitates making subcutaneous cuts in the tissue. Finally, by removing the obturator completely and attaching a syringe, fluid may be introduced into the knee. Each of these functions may be undertaken without removing the instrument and making successive incisions.

BRIEF DESCRIPTION OF THE DRAWING

The invention disclosed herein will be better understood with reference to the following drawings of which:

FIG. 10 is a side elevation of the handle of FIG. 9 attached to a syringe;

FIG. 11 is a cross-sectional view of the handle of a preferred embodiment of the present invention with the obturator partially withdrawn;

FIGS. 12A and 12B are side and end cross sectional views, respectively, of a preferred embodiment of part of the present invention, FIG. 12B being taken along the line 12B—12B of FIG. 12A, and FIG. 12A being taken along the line 12A—12A of FIG. 12B;

FIGS. 13A and 13B are side and end cross sectional views, respectively, of a preferred embodiment of part of the present invention, FIG. 13B being taken along the line 13B—13B of FIG. 13A, and FIG. 13A being taken along the line 13A—13A of FIG. 13B; and FIGS. 14A and 14B are side and end cross sectional views, respectively, of a preferred embodiment of the present invention in the retractor mode, FIG. 14B being taken along the line 14B—14B of FIG. 14A, and FIG. 14A being taken along the line 14A—14A of FIG. 14B.

DETAILED DESCRIPTION OF THE PREFERRED EMBODIMENTS

Figure 1:
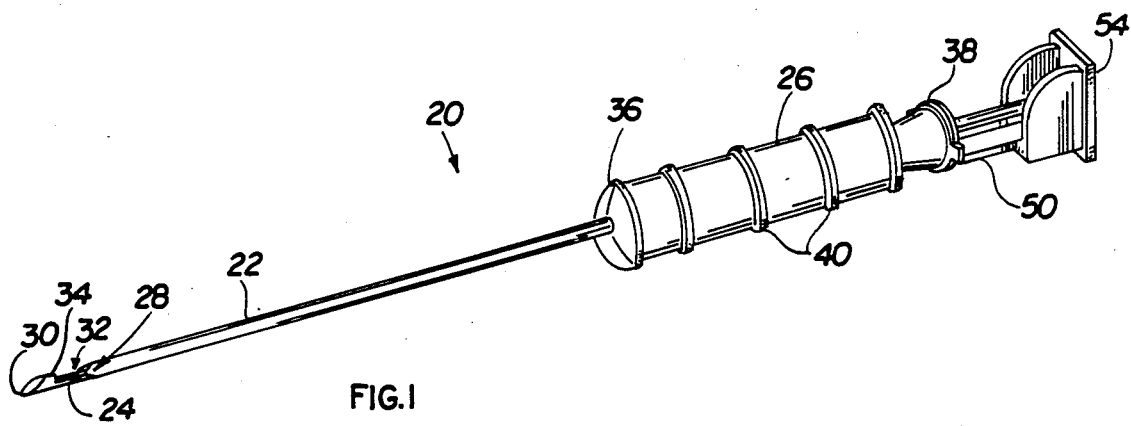
FIG. 1 is a perspective view of a preferred embodiment of a surgical instrument in accordance with the present invention showing the obturator advanced out of the sheath in the retractor mode.

Referring to FIG. 1, there is shown an improved tissue retractor 20 having a hollow cylindrical sheath 22 and a pointed cylindrical obturator 24 slidingly contained in a close-fitting relationship within the sheath. The sheath 22 and obturator 24 are both made of a suitable surgical metallic material as is known in the art. A handle 26 is attached to one end of the hollow sheath 22, and the opposite end of the sheath, indicated by 28, is pointed. Near, but not at the obturator's pointed end 30, the obturator includes a reduced cross-sectional area 32. The surface of the obturator 24 between the pointed end 30 and the reduced cross-sectional area 32 includes an acute angle which forms a barb 34.

As shown in FIG. 1, the obturator 24 has been partially extended out of the sheath 22. This configuration is known as the "retractor" mode of the invention. In this mode, the reduced cross-sectional area 32 may be pressed against tissue and the tissue will be retained in the reduced cross-sectional area 32 against the barb 34, and may be retracted.

As shown, the handle 26 has a generally cylindrical shape which is comfortable to grasp and permits accurate control of the tissue retractor 20. A finger stop 36 is provided at one end of the handle for added control. A nozzle 38, the function of which will be hereinafter described, is provided at the opposite end of the handle. As shown, the handle includes several ridges 40 which further improve handling and control.

Figure 2A:
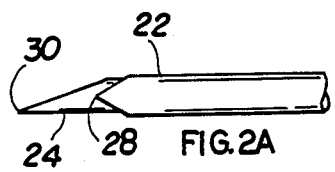
FIGS. 2A-2D are four views of part of a surgical instrument in accordance with a preferred embodiment of the present invention showing respectively: a side elevation view of the instrument in the probe mode, a side elevation view of the instrument in the retractor mode, a plan view of the instrument in the retractor mode, and a plan view of the instrument in the distender mode.

The manner in which the surface of the sheath 22 and the obturator 24 cooperate to form the various modes of the invention can be best seen from FIGS. 2A-2D. In FIG. 2A, the tip of the invention is shown in what may be known as the "probe" mode. In this mode, the obturator 24 is withdrawn partially into the sheath 22 so that the sheath fully encloses the reduced cross-sectional area 32 of the obturator. The surface of the sheath 22 and of the obturator 24 cooperate to form a generally smoothly shaped surface which will not snag or tear tissue and will act as a "needle" for piercing tissue and probing the interior of a knee joint prior to making larger incisions. The ends of the obturator 24 and the sheath 22 may be beveled to form an even smoother surface.

Figure 2B:
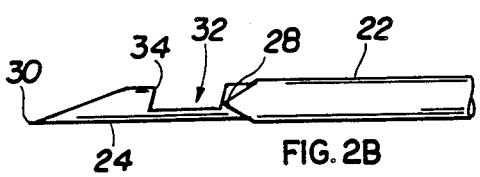
Figure 2C:
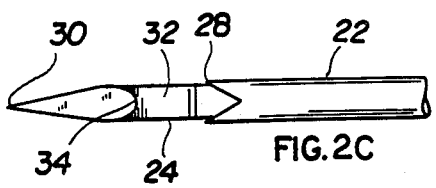

In FIGS. 2B and 2C, the "retractor" mode of the invention is shown. FIG. 2C shows the tip of the tissue retractor 20 rotated 90° along the longitudinal axis of FIG. 2B. In this mode, the obturator 24 has been advanced sufficiently out of the sheath 22 to expose the barb 34 and the reduced cross-sectional area 32. The reduced cross-sectional area 32 may now be pressed against tissue (not shown), and the tissue will be retained within the area 32 by the barb 34. With tissue thus held in place, the handle of the tissue retractor may be pulled gently and the tissue will be taught and retracted and available for making the subcutaneous cut. After the cut is made, disengagement of the tissue from the tissue retractor is simple. One merely advances the obturator 24 while maintaining the position of the sheath 22 to relieve the tension in the tissue, then advances the sheath 22 along the obturator 24 to cover the reduced cross-sectional area 32. As shown, the sheath 22 has two bevels which form the points 28 which further help to disengage tissue when the sheath is advanced. The entire tissue retractor may then be withdrawn without snagging or tearing tissue.

Figure 2D:
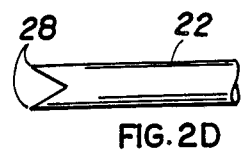

In FIG. 2D, the obturator has been withdrawn completely into the sheath 22. The pointed end of the sheath, here shown as two points 28, can engage tissue and may be used to stretch tissue. This is known as the "distender" mode of the invention. To use the tissue retractor in this mode, the invention would be first introduced into the knee joint while in the probe mode, then the obturator would be at least partly withdrawn. The points 28 would engage tissue and gentle pressure on the handle would place the tissue into stretching tension for making the subcutaneous cut.

Figure 3A:
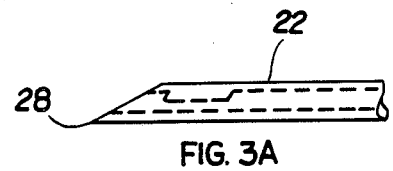
FIGS. 3A and 3B are two views of part of another preferred embodiment of the present invention showing a side elevation schematic of the instrument in the probe mode, and a side elevation of the instrument in the retractor mode, respectively.
Figure 3B:
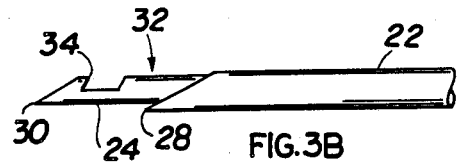

Another preferred embodiment of the tip of the present invention is shown in FIGS. 3A and 3B. In this embodiment, the pointed end of the sheath 28 and the pointed end of the obturator 30 are both formed by a steeply slanted bevel. In this embodiment, the invention is shown in the probe mode in FIG. 3A and in the retractor mode in FIG. 3B. By withdrawing the obturator 24, the instrument may be used in the distender and fluid introducing modes.

Figure 4A:
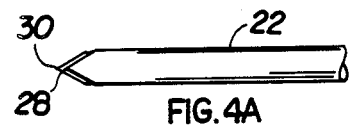
FIGS. 4A and 4B are two views of part of another embodiment showing a side elevation of the instrument in the probe mode, and a side elevation of the instrument in the retractor mode, respectively.
Figure 4B:
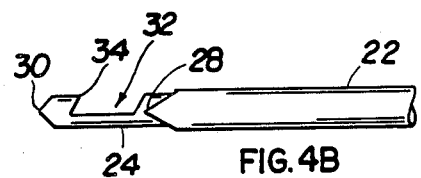

The tip of another embodiment is shown in FIGS. 4A and 4B. This embodiment is similar to that shown in FIGS. 2A–2D except that the point 30 of the obturator 24 is formed by a double-cut and is along the longitudinal axis. In all important respects, this embodiment performs the same functions in a similar manner as that shown in FIGS. 2A–2D.

Figure 5A:
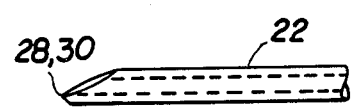
FIGS. 5A and 5B are two views of part of another embodiment showing a side elevation schematic of the instrument in the probe mode, and a side elevation view of the instrument in the retractor mode, respectively.
Figure 5B:
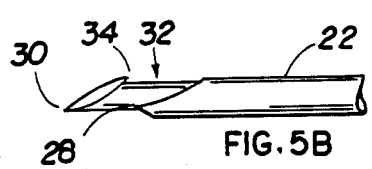

The tip of the embodiment of the invention shown in FIGS. 5A and 5B has a barb 34 which extends flush with the outer surface of the sheath 22. The reduced cross-sectional area 32 extends from the barb along the remaining length of the obturator 24. Since the barb 34 extends flush with the outer surface of the sheath 22, the obturator 24 cannot be fully withdrawn into the sheath 22 and the invention cannot be used in the distender mode. Additionally, as will be more fully explained hereinafter, because the obturator 24 cannot be removed from the sheath 22, this embodiment of the invention cannot be used in the "fluid introducing" mode. In this embodiment, the points 28 of the sheath 22 have been formed by a double-cut. Note that when this embodiment is in the probe mode as shown in FIG. 5A, the sheath points 28 and the obturator point 30 coincide, forming an especially smooth surface.

Figure 6A:
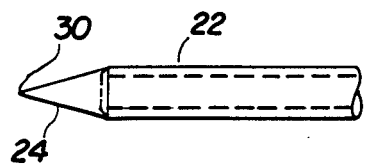
FIGS. 6A-6D are four views of part of another embodiment showing respectively: a side elevation schematic of the instrument in the probe mode, a side elevation view of the instrument in the probe mode, a side elevation of the instrument in the retractor mode, and a partial cross-sectional side elevation view of the instrument in the retractor mode.
Figure 6B:
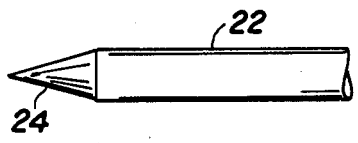
Figure 6C:
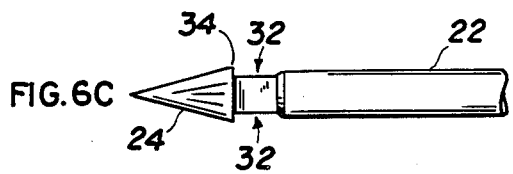
Figure 6D:
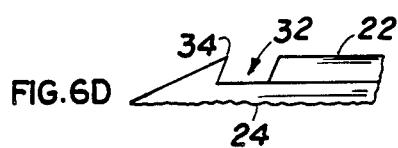

In the embodiment shown in FIGS. 6A–6D, the point 30 of the obturator 24 takes a conical shape, and the barb 34 extends around the circumference of the obturator. Similarly, the reduced cross-sectional area 32 takes a cylindrical shape and also extends completely around the obturator. This embodiment is similar to those shown in FIGS. 5A–5B in that the obturator 24 may not be withdrawn from the sheath 22 and the invention may not take either the distender or fluid introducing modes. Although the unavailability of these two modes of use is somewhat disadvantageous, this embodiment is useful as the barb 34 is flush with the outer surface of the obturator 24 completely around the instrument and forms a very smooth external surface when in the probe mode as shown in FIGS. 6A and 6B.

Having thus described the operation of the obturator and the sheath at the tip end of my tissue retractor, I will now describe the structure and operation at the handle end of my invention.

Figure 7:
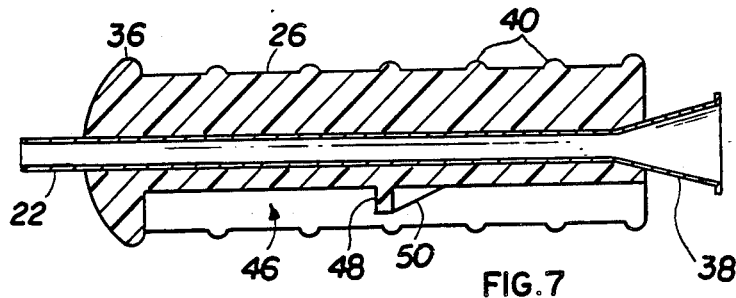
FIG. 7 is a cross-sectional view of a handle of a preferred embodiment of the present invention.
Figure 8:
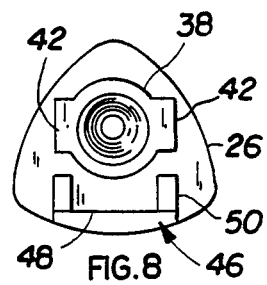
FIG. 8 is an end elevation view of a preferred embodiment of the present invention.
Figure 9:
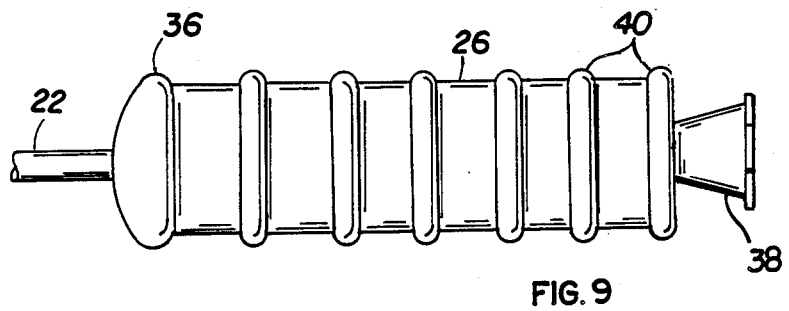
FIG. 9 is a side elevation of the handle of FIG. 7.

Referring to FIGS. 7, 8 and 9, a preferred embodiment of the handle 26, including the finger stop 36, the nozzle 38, and the ridges 40 is shown. Although many materials would be satisfactory, molded plastic is preferable for fabrication of the handle 26.

As shown, the hollow sheath 22 passes through the handle 26 and leads to and connects with the nozzle 38. As the opposite end of the sheath 22 is open to permit the obturator 24 to extend therethrough, it can be clearly seen that a fluid supplied to the nozzle end of the tissue retractor, under sufficient pressure, will pass through the entire length of the sheath and be introduced into the knee joint being operated upon. Thus, when the obturator is removed, the invention may be used in its "fluid introducing" mode.

The nozzle 38 has a generally conical shape, and acts as a funnel. The open end of the nozzle 38 is preferably chosen according to the size of a typical syringe. A pair of tabs 42 are provided at the end of the nozzle 38 to permit the nozzle to be threaded onto the syringe. A syringe 44 connected to the handle 26 of the present invention is shown in FIG. 10. Syringes commonly include threads and such a syringe-to-nozzle connection as shown here is known in the art.

One side of the handle 26 includes a trough 46 which can best be seen from FIGS. 7 and 8. A bridge 48 spans the trough 46 at a predetermined location. A pair of ramps 50 are provided at either end of the bridge 48 and abut the inner walls of the trough 46.

The trough 46, bridge 48, and ramps 50 serve to maintain a fixed position of the obturator 24 within the sheath 22, as can best be understood with reference to FIG. 11. In this figure, the obturator 24 is shown partially withdrawn from the sheath 22. The obturator 24 is affixed to an obturator guide member 52 which, like the handle 26, may be fabricated from molded plastic. One end of the guide member 52 forms a finger stop 54. A pair of ribs 56 securely hold the end of the obturator 24. The guide member 52 also includes a beam member 58 having a rounded projection 60 and an end stop 62. The beam member 58 and the bridge 48 with its ramps 50 cooperate to reliably maintain the position of the obturator 24 within the sheath 22.

As shown, the obturator 24 is partially withdrawn into the sheath 22. Pushing on the finger stop 54 would advance the obturator 24 out of the sheath 22 until the end stop 62 advances within the trough 46 and contacts the ramps 50. Pushing further causes the beam member 58 to deflect slightly as the end stop 62 travels along the ramps 50. At the position where the end stop 62 has traveled over the ramps 50 and passed the bridge 48, but before the projection 60 has engaged the bridge 48, the obturator is reliably held in place and the invention assumes the probe mode. By pushing further on the finger stop 54, the projection 60 travels past the bridge 48, transforming the invention into its retractor mode. Upon completion of the task of tissue retraction, the apparatus of the present invention may be transformed back into its probe mode by gently pulling on the finger stop 54 and causing the projection 60 to pass back over the bridge 48. To withdraw the obturator 24 further from the sheath 22, the surgeon need only gently push on the beam member 58 deflecting it so that the end stop 62 can pass by the bridge 48. The obturator 24 may then be fully withdrawn from the sheath 22.

Another preferred embodiment of the invention is shown in FIGS. 12A-14B. In this embodiment, the tip of the sheath 22 and obturator 24 are similar to those illustrated in FIGS. 3A and 3B. It has been found that this form of the tip is the easiest to reliably manufacture which resists snagging tissue when in the probe mode.

Rather than a one piece handle as described above, the handle 26' is formed by two concentric tubes. An outer tube 64 (herein called the obturator tube) is connected to the obturator 24 and can be most clearly seen from FIG. 12A. The inner tube is a sheath tube 66 and can best be seen from FIG. 13A. Along one side of the obturator tube 64 is a groove 68 which can also be seen in FIG. 12B. A ridge 70 projects from one side of the sheath tube 66 as can be seen in FIGS. 13A and 13B. The ridge 70 fits within the groove 68 and serves to maintain rotational alignment of the obturator 24 with respect to sheath 22. Prohibiting twisting between the sheath and obturator in this manner is important so that the surgeon knows with certainty which side of the obturator to press against the tissue for retraction.

The side of the sheath tube 66 opposite the ridge 70 includes three notches 72a, 72b and 72c. These notches cooperate with a hinged locking member 74 in the obturator tube 64 to fix the position of the obturator 24 within the sheath 22 at predetermined locations. The locking member 74, shown in FIG. 12A angled away from the obturator tube 64, hinges into and out of the obturator tube 64.

The locking member 74 includes a projection 78 which fits into the notches 72a, 72b and 72c. The projection 78 is rounded so that sliding the obturator tube 68 along the sheath tube 70 will cause the locking member 74 to disengage from its notch. The three notches 72a, 72b and 72c shown, correspond to three of the modes of the invention. Notch 72a, for which the sheath tube 66 is most extended from the obturator tube 64 corresponds to the distender mode of the invention as the obturator 24 is completely enclosed by the sheath 22. The middle notch, notch 72b, corresponds to the probe mode of the invention as at this point, the surface of the obturator 24 is even with the surface of the sheath 22. The third notch 72c corresponds to the retractor mode of the invention as the obturator 24 extends out of the sheath 22. This retractor mode is illustrated in FIG. 14A. The obturator 24 may be completely removed from the sheath 22 and the sheath tube 66, to utilize the invention in the fluid introducing mode.

To utilize this embodiment for fluid introduction, a syringe (not shown) would be attached to the nozzle 38, which is in fluid communication with a plenum 80 and the sheath 22. A front end 82 of the plenum 80 is tapered so that the obturator 24 may be easily re-inserted into the sheath 22.

It is useful to be able to rotate the tissue retractor to any desired orientation. In order to provide a firm and positive grip to permit such rotation, the end of the obturator tube 64 is fluted as shown in FIG. 14B, and the sheath tube 66 includes a pair of flat-bottomed finger depressions 84.

The preferred embodiment of the invention depicted in FIGS. 12A-14B is particularly easy and convenient to use. By grasping the sheath tube 66 with a thumb and forefinger in finger depressions 84, and holding the fluted end of the obturator tube 68 in the palm of the hand, the instrument may be easily alternated between the probe, retractor and distender modes by merely moving the thumb and forefinger back and forth. Once the instrument is positioned in the correct mode, the surgeon may simply slide his thumb back and press the locking member 74 into the proper notch 72a, 72b or 72c. To confirm that instrument is in the proper mode, the surgeon can easily visually verify that the proper notch has been engaged. Additionally, the surface of sheath tube 66 may be marked with letters such as "R", "P" and "D" (for retractor, probe and distender, respectively) which become covered or uncovered as the sheath tube 66 moves in and out of the obturator tube 68.

It is thus seen that the objects of my invention have been achieved and other advantageous results attained in that there has been disclosed a surgical apparatus which is able to put flaps and tags of tissue under either retracting or stretching tension for cutting, which is capable of performing several functions within a single incision, which may be readily and accurately manipulated under arthroscopic visualization, which is useful in introducing fluid into a joint, which may be used as a probe within a joint, and which is inexpensive and easy to fabricate.

While the several figures show specific preferred embodiments of my improved tissue retractor, it is to be understood that such structure is not intended as any limitation, as the present invention may take different forms.

Various modifications of the present invention will become apparent to those skilled in the art from the foregoing description and accompanying drawings. For example, while a cylindrical obturator and sheath have been shown and described, it would also be useful to provide members with other cross-sectional shapes. Such modifications are intended to fall within the scope of the appended claims.

What is claimed is:

1. An apparatus for use during arthroscopic surgery on tissue comprising:
   a substantially tubular sheath having a hollow interior and an outer surface, and
   an obturator having an outer surface slidingly contained within said sheath, said obturator having a first end which is sharp and pointed, and a reduced cross-sectional area near said first end, the outer surface of said obturator between said first end and said reduced cross-sectional area being without a slicing edge, so that the tissue may be retained against said reduced cross-sectional area without slicing through the tissue when said obturator is advanced out of said sheath.

2. The apparatus of claim 1 wherein said tubular sheath has a first end which is sharply bevelled so that said sheath may disengage the tissue from said reduced cross-sectional area when said sheath is advanced along said obturator, so that the tissue may be engaged by said sheath when said obturator is withdrawn.

3. The apparatus of claim 2 further comprising means attached to said obturator and said sheath for maintaining a first axial position of said obturator relative to said sheath, and means for permitting linear displacement of said obturator relative to said sheath from said first axial position.

4. The apparatus of claim 3 wherein said reduced cross-sectional area is enclosed within said sheath when said first axial position is maintained so that the outer surface of said obturator at said first end and the outer surface of said sheath cooperate to form a generally smoothly shaped surface in the vicinity of the interface between said sheath and said obturator, whereby the tissue may be pierced by the apparatus without catching, and the apparatus may be withdrawn from the tissue without catching.

5. The apparatus of claim 4 further comprising means attached to said obturator and said sheath for maintaining an additional axial position of said obturator relative to said sheath, other than said first axial position, so that said reduced cross-sectional area is exposed out of said sheath when said additional axial position is maintained, said additional axial position maintaining means being aligned with said first axial position maintaining means so that changing position from one said axial position maintaining means to the other said axial position maintaining means is performed by linearly sliding said obturator relative to said sheath.

6. The apparatus of claim 4 further comprising means for maintaining an additional axial position of said obturator relative to said sheath so that the first end of said obturator is enclosed within said sheath when said additional axial position is maintained, said additional axial position maintaining means being aligned with said first axial position maintaining means so that changing position from one said axial position maintaining means to the other said axial position maintaining means is performed by linearly sliding said obturator relative to said sheath.

7. The apparatus of claim 1 further comprising a handle attached to an end of said sheath.

8. The apparatus of any of claims 3–6 further comprising a handle attached to the end of said sheath opposite said sharp end, said handle including each said axial position maintaining means and said means for permitting linear displacement.

9. The apparatus of claim 1 further comprising:
an obturator tube attached to the end of said obturator opposite said first end, and
a sheath tube attached to an end of said sheath and slidingly contained within said obturator tube so that said sheath tube and said obturator tube cooperate to form a handle.

10. The apparatus of any of claims 3–6 further comprising:
an obturator tube attached to the end of said obturator opposite said first end;
a sheath tube attached to the end of said sheath opposite said first end and slidingly contained within said obturator tube so that said sheath tube and said obturator tube cooperate to form a handle; and
wherein said handle includes each said axial position maintaining means.

11. The apparatus of claim 1 further comprising means for attaching said sheath to fluid introducing means whereby said sheath provides a fluid flow passage from said fluid introducing means to the tissue.

12. The apparatus of claim 11 wherein said attaching means includes a nozzle having means to engage the threads of a syringe.

13. Apparatus for use during arthroscopic surgery on tissue comprising, in combination:
means for tensioning tissue in a first direction without slicing through the tissue, and
means for tensioning tissue in a second direction, co-axial with and opposite to said first direction, whereby both said tensioning means may be slidingly adjusted relative to each other so that together they cooperate to form means for piercing tissue.

14. The combination of claim 13 whereby said second direction tensioning means comprises means for introducing a fluid into said tissue.

15. The combination of claim 13 wherein said means for tensioning tissue in said first direction includes a barbed obturator.

16. The combination of claim 13 wherein said means for tensioning tissue in said first direction includes an obturator having an outer surface and a first end which is pointed and a reduced cross-sectional area near said end, the surface of said obturator between said pointed end and said reduced cross-sectional area being without a slicing edge.

17. The combination of claim 13 wherein said means for tensioning tissue in said second direction includes a sheath with a sharp end.

18. The combination of claim 13 wherein said means for piercing tissue includes a pointed obturator slidingly contained within a sheath, wherein the axial position of said obturator within said sheath may be adjusted by linearly sliding said obturator to a fixed position.

19. The combination of claim 14 wherein said fluid introducing means includes a hollow sheath, and a nozzle at one end of said hollow sheath.

20. the combination of claim 19 wherein said nozzle includes means for attaching a syringe.

* * * * *